United States Patent [19]

Arnoldy et al.

[11] Patent Number: 5,364,957
[45] Date of Patent: Nov. 15, 1994

[54] CARBONYLATION PROCESS USING PALLADIUM PHOSPHINE CATALYST

[75] Inventors: Peter Arnoldy; Antoon P. M. Kremers, both of Amsterdam, Netherlands

[73] Assignee: Shell Oil Company, Houston, Tex.

[21] Appl. No.: 45,290

[22] Filed: Apr. 8, 1993

[30] Foreign Application Priority Data

Apr. 8, 1992 [EP] European Pat. Off. ........ 92201014.5

[51] Int. Cl.$^5$ .............................................. C07C 67/36
[52] U.S. Cl. ..................................... 560/207; 560/233
[58] Field of Search ................................ 560/207, 233

[56] References Cited

U.S. PATENT DOCUMENTS

| | | | |
|---|---|---|---|
| 2,586,341 | 2/1952 | Hyson | 260/533 |
| 3,009,948 | 11/1961 | Lautenschlager et al. | 260/486 |
| 3,023,237 | 2/1962 | Reppe et al. | 260/533 |
| 3,025,322 | 3/1962 | Smolin et al. | 260/533 |
| 3,466,324 | 9/1969 | Kunichika et al. | 260/486 |
| 3,496,221 | 2/1970 | Happel et al. | 260/486 |
| 3,709,927 | 1/1973 | Kunichika et al. | 260/486 |
| 3,755,421 | 8/1973 | Fenton et al. | 260/484 |
| 3,812,175 | 5/1974 | Heppel et al. | 260/486 |
| 4,416,823 | 11/1983 | Foley | 260/410.9 |
| 4,447,640 | 5/1984 | Eickholt | 560/207 |
| 4,480,116 | 10/1984 | Clonce et al. | 560/4 |
| 4,739,109 | 4/1988 | Drent | 560/207 |
| 4,739,110 | 4/1988 | Drent | 560/207 |
| 4,786,443 | 11/1988 | Drent et al. | 260/549 |
| 4,940,787 | 7/1990 | Drent | 536/124 |
| 5,028,576 | 7/1991 | Drent et al. | 502/167 |
| 5,099,062 | 3/1992 | Drent et al. | 560/207 |
| 5,103,043 | 4/1992 | Drent et al. | 560/207 |
| 5,124,300 | 6/1992 | Drent | 502/167 |
| 5,158,921 | 10/1992 | Drent et al. | 502/167 |
| 5,166,116 | 11/1992 | Drent et al. | 502/167 |
| 5,166,411 | 11/1992 | Drent | 560/207 |
| 5,177,253 | 1/1993 | Drent et al. | 560/207 |
| 5,179,225 | 1/1993 | Drent et al. | 560/207 |

FOREIGN PATENT DOCUMENTS 0106379 4/1984 European Pat. Off. .
0386833 9/1990 European Pat. Off. .
495547 7/1992 European Pat. Off. .

*Primary Examiner*—Paul J. Killos

[57] ABSTRACT

The invention relates to a process for the carbonylation of an olefinically or acetylenically unsaturated hydrocarbon compound by reaction with carbon monoxide and a hydroxy compound in the presence of a catalyst system comprising a source of cationic palladium, a source of phosphine and a protonic acid, which reaction is carried out in the presence of a free radical inhibitor.

10 Claims, No Drawings

_5,364,957_

CARBONYLATION PROCESS USING PALLADIUM PHOSPHINE CATALYST

FIELD OF INVENTION

This invention relates to a process for the carbonylation of an olefinically or acetylenically unsaturated hydrocarbon compound by reaction with carbon monoxide and a hydroxy compound in the presence of a catalyst system comprising a source of cationic palladium, a source of phosphine and a protonic acid.

BACKGROUND OF THE INVENTION

A carbonylation process of olefinically or acetylenically unsaturated hydrocarbon compound with carbon monoxide and hydroxy compound provides a versatile tool for the economic production of various chemicals starting from readily available unsaturated hydrocarbon feedstock. The carbonylation reaction may be represented by the equation:

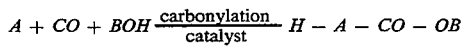

where A represent the unsaturated hydrocarbon compound and BOH represents the hydroxy compound, such as water (B=H), alcohols (B=R), and carboxylic acids (B=RCO). Generally, olefinic precursors provide saturated products, whereas acetylenic precursors provide olefinic products; multiple carbonylations such as producing saturated products from acetylenic precursors not being excluded. Depending on the nature of the hydroxy compound BOH, various functionalized products, including carboxylic acids, esters, and anhydrides can be obtained.

It has been found that catalytic systems containing cationic palladium, a phosphine ligand, and a protonic acid are well suited for carbonylation reactions. These catalyst systems allow the carbonylation reaction to proceed at high rate under mild conditions in respect of temperature and carbon monoxide pressure. By dedicated choice of the type of phosphine and the nature of the protonic acid, extremely high selectivities to specific desired product could be obtained. For further details of specific carbonylation reactions thus catalyzed reference is made to EP-106379-B, U.S. Pat. No. 4,739,109, U.S. Pat. No. 4,739,110, U.S. Pat. No. 4,940,787, U.S. Pat. No. 4,786,443, U.S. Pat. No. 5,099,062, U.S. Pat. No. 5,158,921, U.S. Pat. No. 5,028,576, U.S. Pat. No. 5,103,043, U.S. Pat. No. 5,158,921, U.S. Pat. No. 5,124,300, U.S. Pat. No. 5,166,411, U.S. Pat. No. 5,166,116, U.S. Pat. No. 5,177,253, U.S. Pat. No. 5,179,225. The low temperatures of these carbonylation reactions are particularly advantageous in that the usual problem of polymerization as side reaction in preparations and/or purifications involving vinylic precursors or products does not occur to an appreciable extent.

Generally, these catalyst systems should comprise a rather high ratio of moles of phosphine to gram atoms of palladium for securing high conversions at low palladium concentration. The high phosphine content disadvantageously attributes to the waste streams and the economics of the above processes, in particularly when using substituted phosphines for specific selective processes. Therefore, it would be desirable to reduce the phosphine/palladium ratio without affecting the performance of these catalyst systems.

The use of inhibitors in other carbonylation reactions and/or preparation processes for methyl methacrylate (MMA) has been reported. However, in such cases the inhibitor was added for its well-known function of inhibiting polymerization reactions of vinylic compounds, since the processes were carried out at temperatures of about 100° C. or much higher. For example, U.S. Pat. No. 4,447,640 discloses the preparation of MMA by carbonylation of 1,2-dihaloalkanes in the presence of a supported palladium catalyst and an inhibitor at temperatures in the range of 150°–300° C. The specification mentions that homogeneous catalysts comprising a group VIII metal salt in conjunction with a triorganic phosphine can also be used, without providing further detail. The alleged effects of inhibitor addition as elucidated in column 4, lines 7-37, are prevention of polymerization of the product and increase of the active life of the catalyst by prevention of fouling of the catalyst through deposit of carbon thereon. The latter problem would clearly seem to be confined to heterogeneous catalysts. U.S. Pat. No. 4,480,116 discloses the preparation of MMA by acid hydrolysis of acetone cyanohydrin in the presence of 50-3000 ppm of specific inhibitors, particularly during the work up procedures. Again, the alleged effect is prevention of polymerization of MMA product, whereas this publication is silent on any effect on the life of the catalyst. In Example 22 of EP-A-386833, the carbonylation of 3-butynol is carried out in the presence of hydroquinone for preventing polymerization of the methylenolactone product formed. U.S. Pat. No. 4,416,823 discloses the dimeric hydroesterification of 1,3-alkadienes in the presence of a palladium/phosphine/thiol stabilized complex catalyst at preferred temperatures in the range of 80°–120° C. Preferably, the reaction is conducted in the presence of a vinyl polymerization inhibitor to avoid an increased incremental loss of 1,3-butadiene to polymeric by-products. None of these publications give any hint to the reduction of a phosphine/palladium ratio in general carbonylation reactions, let alone the type of carbonylation reaction of the present invention.

It is therefore an object of the present invention to provide a process of carbonylating olefinically or acetylenically unsaturated compounds with carbon monoxide and a hydroxy compound in the presence of a catalyst system comprising a source of cationic palladium, a source of phosphine and a protonic acid with reduced phosphine/palladium ratio.

SUMMARY OF THE INVENTION

According to the invention, a process for the carbonylation of an olefinically or acetylenically unsaturated hydrocarbon compound is provided, comprising reacting the olefinically or acetylenically unsaturated hydrocarbon compound with carbon monoxide and a hydroxy compound in the presence of a carbonylation catalyst system comprising a source of cationic palladium, a source of phosphine and a protonic acid and a free radical inhibitor.

The present inventive process where the reaction is carried out in the presence of the free radical inhibitor, the catalytic system used in the present process is effective at a lower initial phosphine proportion.

DETAILED DESCRIPTION OF THE INVENTION

It is now believed that some phosphine was inactivated during the previously described carbonylation reaction and that the high ratio of phosphine to palladium in the catalyst system was required for maintaining a sufficient supply of available phosphine during the entire course of the carbonylation reaction. The invention proposes the use of a free radical inhibitor in a process for the carbonylation of an olefinically or acetylenically unsaturated hydrocarbon compound where the olefinically or acetylenically unsaturated hydrocarbon compounds are reacted with carbon monoxide and a hydroxy compound in the presence of a catalyst system comprising a source of cationic palladium, a source of phosphine and a protonic acid for reducing the rate of consumption of the phosphine.

It was surprisingly found, that in the present carbonylation reaction the free radical inhibitor provides a beneficial effect different from its usual effect of inhibiting vinylic polymerization. As a consequence, catalytic systems having a lower phosphine/palladium ratio than used heretobefore, can be used without negative influence to the catalyst life, and therefore the degree of conversion, in the carbonylation process conducted under the same conditions. Accordingly, the invention provides a reduction of costs of phosphine ligands and a reduction of the disposal of the phosphine content of the waste stream of the known process.

The concentration of the free radical inhibitor may vary within wide limits depending on factors such as the duration of the carbonylation, the concentration of trace oxygen, the catalyst concentration and the temperature. For economically attractive carbonylation reactions, the concentration of the free radical inhibitor is preferably in the range of about 0.0005-1% by weight, more preferably in the range of about 0.001-0.1% by weight, based on the total of reaction components. It is an additional advantage of the present invention, that these inhibitor concentrations also will very effectively inhibit any polymerization reaction. At normal process temperatures of about 50° C., this side effect is though advantageous in theory, but of secondary significance in practice.

Free radical inhibitors, sometimes referred to as polymerization inhibitors, suitable for use in the present process are known free radical inhibitors used in conventional polymerization technology, and any such free radical inhibitor can be used in the present process. Representative suitable free radical inhibitors include aromatic hydroxyl compounds, aromatic keto compounds, benzo- and naphthoquinones, phenazines, phenoxazines and phenothiazines. Preferred free radical inhibitors are selected from the group of substituted phenols, including such phenols substituted with further hydroxy groups, for instance hydroquinone. The phenols may carry any further inert substituent, in particular alkyl groups such as methyl and tert.butyl, and include hydroxylated condensed aromatic ring systems, such as naphthol.

Preferable free radical inhibitors include, for example, monohydric phenols, such as 4-methyl-2,6-di-tert-.butylphenol ("butylated methylphenol"), 2,4-dimethyl-6-tert.butylphenol, beta-naphthol, p-methoxyphenol ("methylhydroquinone"); dihydric phenols, such as hydroquinones, naphthohydroquinones, catechols, for instance p-tert.butylcatechol, and trihydric phenols, such as pyrogallol.

Due to the presence of the free radical inhibitor, the catalytic system used in the present process is effective at lower initial phosphine proportion. Accordingly, catalyst systems are advantageous, which comprise, at the start of the reaction, a ratio of moles of phosphine to gram atoms of palladium in the range of from about 2.5 to about 50, preferably of from about 5 to about 30. Higher phosphine proportions do not disturb the reaction, but attenuate the economic benefits achieved by the invention.

The proportion of the protonic acid in the catalyst system related to the initial proportion of phosphine, is suitably in the range of from about 0.5 to about 10. It has been found that the use of an acid/phosphine ratio around one is beneficial to the rate of phosphine consumption, and accordingly it is preferred that the ratio of moles of protonic acid to moles of phosphine is in the range of from about 0.7 to about 1.5.

The olefinically or acetylenically unsaturated compounds to be carbonylated, the suitable sources of cationic palladium, phosphine and protonic acid, the reaction conditions and further experimental details are extensively described in the United States patents mentioned hereinbefore, which are incorporated herein by way of reference.

In summary, olefinically unsaturated hydrocarbons include alkenes, in particular 1-alkenes, having generally 2-20 carbon atoms, which may be straight or branched and may comprise a plurality of double bonds, for example ethene, propene, 1-butene, 2-butene, the isomeric pentenes, hexenes, octenes, and 1,5-cyclooctadiene. Acetylenically unsaturated compounds include alkynes, in particular 1-alkynes, which may be straight or branched unsubstituted and may comprise a plurality of triple bonds or further double bonds, for example ethyne, propyne, and 1-butyne. Suitable hydroxy compounds include water, alcohols, and carboxylic acids, which may be aliphatic, cycloaliphatic or aromatic, preferably contain not more than 20 carbon atoms, and may have more than one hydroxy function. Examples of suitable alcohols include methanol, ethanol, propanol, isobutanol, tert.butanol, stearyl alcohol, phenol, ethylene glycol and glycerol. Examples of suitable carboxylic acids include acetic acid and propionic acid.

Suitable palladium sources include palladium compounds such as salts, for example palladium acetate, and complexes, for example tetrakis-triphenylphosphinepalladium and bistriphenylphosphinepalladium acetate, but also metallic palladium which is solubilized by the acid component of the catalyst system. Suitable phosphines generally include triorganic phosphines, of which the organic substituents independently of each other may be aliphatic, cycloaliphatic, aromatic or heterocyclic and contain 1-10 carbon atoms, for example triphenylphosphine, ethyldiphenylphosphine, dicyclohexylphenylphosphine, 2-pyridyldiphenylphosphine, bis(6-methyl-2pyridyl)phenylphosphine, tri-p-chlorophenylphosphine and tri-pmethoxyphenylphosphine. Preferred phosphines comprise at least one optionally substituted 2-pyridyl group. Suitable protonic acids preferably have a non-coordinating or weakly coordinating anion. Generally, such acids are strong acids having a pKa below about 4.5, more particularly below about 2 (measured at 18° C. in aqueous solution), and include sulfuric acid, sulfonic acids, phosphonic acid and certain carboxylic acids. In the present context, the protonic acid may be generated by interaction of a Lewis acid, such as BF₃, with a proton donor, such as HF, or may be generated in situ. It may also be an acidic ion exchange resin.

The process is conveniently effected in the liquid phase. A separate solvent is not essential. Solvents for optional use in the process include aromatic hydrocarbons, esters, ethers and sulfones. At the preferred concentrations, the free radical inhibitor will readily dissolve in the liquid reaction medium. The present process is conveniently carried out at a temperature in the range of from about 10° to about 130° C. Preferred temperatures are in the range of from about 30° to about 90° C. Convenient pressures are in the range of from about 1 to about 100 bar. The molar ratio between the olefinically or acetylenically unsaturated hydrocarbon compound and the hydroxy compound is not critical, and may vary within a range of about 0.01:1 to 100:1. The quantity of the catalyst system is not critical, and the quantity of palladium may conveniently be in the range of about $10^{-7}$ to about $10^{-1}$ of gram atom palladium per mole of unsaturated compound.

The carbon monoxide required for the process according to the invention may be used in a practically pure form or diluted with an inert gas, for example nitrogen. Also hydrogen may be present, if it is substantially inert in the particular carbonylation reaction.

The catalyst systems used in the present process may be prepared by any convenient method. Thus they may be prepared by combining a separate palladium compound, the phosphine and the protonic acid. Alternatively, they may be prepared by combining a palladium compound and an acid addition salt of the phosphine. Alternatively, they may be prepared from a palladium compound which is a complex of palladium with the phosphine, and the protonic acid. The free radical inhibitor may be introduced into the reaction by any convenient method. It may, for example, be admixed with the catalyst system, or it may be incorporated into one of the precursor feeds.

By way of example, the invention will be demonstrated by reference to the carbonylation of an acetylenically unsaturated compound, more particularly the preparation of an alkyl methacrylate by reaction of propyne with carbon monoxide and an alkanol. Such a process is described in more detail in U.S. Pat. No. 4,940,787, and uses a catalyst system that can be formed from a palladium compound, a protonic acid and an organic phosphine of the general formula $PR_1R_2R_3$, wherein one, two or each of $R_1$, $R_2$ and $R_3$ represent a heterocyclic 5 or 6 atom ring comprising at least nitrogen as hetero atom, which ring is optionally substituted and/or may form part of a larger condensed ring structure that is optionally substituted, and any remaining group $R_1$, $R_2$ or $R_3$ represents an optionally substituted hydrocarbyl group.

At the beginning of the reaction, the liquid carrier mainly comprises methanol besides liquified propyne if the reaction is conducted at increased pressure. In the course of the reaction methanol is replaced by methyl methacrylate product further acting as the liquid carrier or solvent for the reaction mixture. In a continuously conducted process, part of the reaction feed consist of a recycled methyl methacrylate/methanol azeotrope stream, and accordingly in each stage of the reaction methyl methacrylate is present.

EXAMPLE

Representative stability tests were carried out by preparing solutions of the indicated molar amounts of the catalyst components in mixtures of methyl methacrylate (MMA) and methanol (MeOH) at the indicated weight ratios or in methanol only. Palladium acetate was used as source of palladium, diphenyl 2-pyridyl phosphine as the ligand and methane sulfonic acid as the acid components of the catalyst system. In tests Nos. 1–3, 5, 6 and 8, furthermore the indicated amount of the indicated type of free radical inhibitor was added. Tests Nos, 4 and 7 are for reference purposes. The solutions were stored for 24 hours under a gaseous medium and at a temperature as indicated. Thereupon, the solutions were analyzed on their content of phosphinoxide relative to the total of phosphorus compounds, phosphine and phosphinoxide. The initial oxide content of the phosphine sample used in theses experiments was 2.4% mol.

The results of the tests are mentioned below. It is seen that the presence of a free radical inhibitor increases the life time of the catalyst system. The effect is particularly pronounced, if the reaction solvent comprises MMA even under a nitrogen atmosphere.

| Test (No.) | 1 | 2 | 3 | 4 | 5 | 6 | 7 | 8 |
|---|---|---|---|---|---|---|---|---|
| MMA (% wt) | 46.8 | 48.6 | 49.3 | 50.2 | 47.4 | 48.8 | — | — |
| MeOH (% wt) | 53.2 | 51.4 | 50.7 | 49.8 | 52.6 | 51.2 | 100 | 100 |
| Medium | $N_2$ | $N_2$ | $N_2$ | $N_2$ | $N_2$ | $N_2$ | air | air |
| Pd (mmol/kg) | 0.23 | 0.12 | 0.11 | 0.11 | 0.12 | 0.11 | 0.21 | 0.23 |
| Ligand (mmol/kg) | 2.41 | 1.20 | 1.16 | 1.16 | 1.23 | 1.11 | 2.84 | 2.92 |
| Acid (mmol/kg) | 5.06 | 2.38 | 2.40 | 2.28 | 2.44 | 2.24 | 1.31 | 1.22 |
| H/L (mol/mol) | 2.1 | 2.0 | 2.1 | 2.0 | 2.0 | 2.0 | 0.46 | 0.42 |
| L/Pd (mol/mol) | 10 | 10 | 10 | 10 | 10 | 10 | 14 | 13 |
| Inhibitor type*) | HQ | HQ | MEHQ | — | HQ | BMP | — | MEHQ |
| (mmol/kg) | 4.94 | 4.68 | 9.02 | — | 0.97 | 2.25 | — | 3.01 |
| Temp. (°C.) | 45 | 45 | 45 | 45 | 45 | 45 | 20 | 20 |
| Oxide**) t = 20 (% mol) | 13.1 | 10.4 | 14.5 | 90.0 | 21.7 | 15.3 | 16.5 | 6.8 |

*)HQ = hydroquinone; MEHQ = methylhydroquinone; BMP = butylated methylphenol.
**)molar proportion of phosphinoxide relative to total P compounds present; initial oxide content of ligand: 2.4% mol.

We claim:
1. In a process for the carbonylation of an olefinically or acetylenically unsaturated hydrocarbon compound by reacting the olefinically or acetylenically unsaturated hydrocarbon compound with carbon monoxide and a hydroxy compound in the presence of a carbonylation catalyst system comprising a source of cationic palladium, a source of phosphine and a protonic acid, the improvement which comprises carrying out the reaction in the presence of a free radical inhibitor and a initial ratio of moles of phosphine to gram atoms of palladium within the range of from about 2.5 to about 50.

2. The process of claim 1 wherein the concentration of the free radical inhibitor is within the range of about 0.0005 to about 1% by weight.

3. The process of claim 2 wherein the concentration of the free radical inhibitor is within the range of about 0.001 to about 0.1% by weight.

4. The process of claim 2 wherein the free radical inhibitor is selected from the group consisting of aromatic hydroxyl compounds, aromatic keto compounds, benzoquinones, naphthoquinones, phenazines, phenoxazines and phenothiazines.

5. The process of claim 3 wherein the free radical inhibitor is a substituted phenol.

6. The process of claim 2 wherein the initial ratio of moles of phosphine to gram atoms of palladium is within the range of from about 5 to about 30.

7. The process of claim 1 wherein the initial ratio of moles of protonic acid to moles of phosphine is within the range of from about 0.5 to about 10.

8. The process of claim 7 wherein the initial ratio of moles of protonic acid to moles of phosphine is within the range of from about 0.7 to about 1.5.

9. The process of claim 1 wherein an acetylenically unsaturated hydrocarbon compound is carbonylated.

10. The process of claim 9 wherein propyne is reacted with carbon monoxide and an alkanol to form an alkyl methacrylate.

* * * * *